(12) United States Patent
Okada (10) Patent No.: US 8,357,082 B2
(45) Date of Patent: Jan. 22, 2013

(54) ENDOSCOPIC ATTACHMENT, ENDOSCOPIC TREATMENT INSTRUMENT, AND ENDOSCOPE SYSTEM

(75) Inventor: Tsutomu Okada, Tokyo (JP)

(73) Assignee: Olympus Corporation (JP)

( * ) Notice: Subject to any disclaimer, the term of this patent is extended or adjusted under 35 U.S.C. 154(b) by 800 days.

(21) Appl. No.: 11/911,279

(22) PCT Filed: Mar. 20, 2006

(86) PCT No.: PCT/JP2006/305495
§ 371 (c)(1),
(2), (4) Date: Oct. 22, 2008

(87) PCT Pub. No.: WO2006/112231
PCT Pub. Date: Oct. 26, 2006

(65) Prior Publication Data
US 2009/0043154 A1    Feb. 12, 2009

(30) Foreign Application Priority Data

Apr. 14, 2005   (JP) ................. 2005-116943

(51) Int. Cl.
*A61B 1/00*           (2006.01)
(52) U.S. Cl. ......... 600/127; 600/104; 600/129; 600/153
(58) Field of Classification Search .................. 600/104, 600/127–129, 153
See application file for complete search history.

(56) References Cited

U.S. PATENT DOCUMENTS

| 4,742,817 | A |   | 5/1988 | Kawashima et al. | |
|---|---|---|---|---|---|
| 4,809,678 | A | * | 3/1989 | Klein | 600/121 |
| 5,201,908 | A | * | 4/1993 | Jones | 600/123 |
| 5,386,817 | A | * | 2/1995 | Jones | 600/104 |
| 5,486,154 | A | * | 1/1996 | Kelleher | 600/104 |
| 5,630,795 | A | * | 5/1997 | Kuramoto et al. | 604/30 |
| 6,059,719 | A | * | 5/2000 | Yamamoto et al. | 600/127 |
| 7,918,783 | B2 | * | 4/2011 | Maseda et al. | 600/104 |

(Continued)

FOREIGN PATENT DOCUMENTS

| JP | 8-168492 | 7/1996 |
|---|---|---|
| JP | 2000-342516 | 12/2000 |

(Continued)

OTHER PUBLICATIONS

Search Report issued by European Patent Office on Dec. 27, 2010 in connection with corresponding European patent application No. EP 06 72 9463.

(Continued)

*Primary Examiner* — Matthew J Kasztejna
(74) *Attorney, Agent, or Firm* — Ostrolenk Faber LLP (57) ABSTRACT

An endoscope system has an endoscope; an attachment for the endoscope, having a non-circular irregularly shaped hole that communicates with an opening of a channel of the endoscope and attached to a forward end of an insertion section of the endoscope; and a treatment instrument for the endoscope, having a flexible tube and a treatment section. An extension/retraction section having a non-circular cross section corresponding to the shape of an opening of the irregularly shaped holes is provided at a forward end of the flexible tube, and the irregularly shaped hole restricts rotation of the flexible tube. Further, the treatment section has directivity about its axis relative to the flexible tube and its rotation is restricted.

4 Claims, 10 Drawing Sheets

U.S. PATENT DOCUMENTS

| | | |
|---|---|---|
| 2002/0035311 A1 | 3/2002 | Ouchi |
| 2003/0191365 A1 | 10/2003 | Kobayashi .................... 600/127 |
| 2005/0043584 A1 | 2/2005 | Nozue |

FOREIGN PATENT DOCUMENTS

| | | |
|---|---|---|
| JP | 2000-354581 | 12/2000 |
| JP | 2001-275933 | 10/2001 |
| JP | 2002-112946 | 4/2002 |
| JP | 3482022 | 10/2003 |
| JP | 2005-80866 | 3/2005 |
| WO | WO 94/22358 | 10/1994 |
| WO | WO 94/28784 | 12/1994 |

OTHER PUBLICATIONS

PCT International Search Report and Written Opinion dated Apr. 25, 2006 issued in corresponding PCT International Patent Appln. PCT/JP2006/305495.

* cited by examiner

ENDOSCOPIC ATTACHMENT, ENDOSCOPIC TREATMENT INSTRUMENT, AND ENDOSCOPE SYSTEM

CROSS REFERENCE TO RELATED APPLICATION

The present application is a 35 U.S.C. §§371 national phase conversion of PCT/JP2006/305495, filed Mar. 20, 2006, which claims priority of Japanese Patent Application No. 2005-116943, filed Apr. 14, 2005, the disclosure of which has been incorporated herein by reference. The PCT International Application was published in the Japanese language.

TECHNICAL FIELD

The present invention relates to an endoscopic attachment mounted on a distal end of an inserted portion of an endoscope, an endoscopic treatment instrument assembled into the endoscope, and an endoscope system composed of the endoscopic attachment, the endoscopic treatment instrument, and the endoscope.

Priority is claimed on Japanese Patent Application No. 2005-116943, filed Apr. 14, 2005, the content of which is incorporated herein by reference.

BACKGROUND ART

It is known that an endoscopic treatment instrument is inserted into a channel of an endoscope inserted into a body such that various treatments are performed on a target portion within the body by a treatment portion formed on a distal end of the endoscopic treatment instrument which projects from a distal end of an inserted portion of the endoscope. It is known that the treatment portion is formed in various shapes depending on treatments performed on a target portion. For example, there are provided a loop-shaped high-frequency snare, which is used when a root such as a polyp or the like is tightened and excised, and a hook-shaped knife which is used when a mucosa or the like is excised. In this case, the treatment portion needs to be rotated around an axis of the channel so as to face an appropriate direction with respect to the target portion, or the treatment portion facing an appropriate direction needs to be restricted from being rotated. Accordingly, a method is proposed, in which a side portion of a treatment portion passing through the inside of the channel is fitted into a fitting groove, which is formed in the vicinity of a distal end of a channel and becomes thin toward the distal end, such that the rotation of the treatment portion is restricted (for example, refer to Patent Document 1). Further, a method is proposed in which a direction control member provided in the rear side of a treatment portion of an endoscopic treatment instrument is fitted into a fitting groove within a channel so as to restrict rotation (for example, refer to Patent Document 2). In addition, a method is proposed, in which an endoscopic attachment is mounted on a distal end of an inserted portion of an endoscope, a hood opening portion of the endoscopic attachment is formed in a shape corresponding to the shape of the treatment portion, and the rotation of a treatment portion is restricted by the hood opening portion when the treatment portion passes through the endoscopic attachment (for example, refer to Patent Documents 3 and 4).

However, in the method where the fitting groove is provided inside the channel of the endoscope, the treatment portion or the projecting direction control member corresponding to the fitting groove is inserted into the channel. Therefore, the inner surface of the channel may be damaged. Further, when the rotation is restricted by the direction control member, the opening of the channel is reduced in size at the distal end where the fitting groove is formed, by the area occupied by the fitting groove. Therefore, when a treatment instrument having no direction control member is used in the endoscope, only an endoscopic treatment instrument corresponding to the shape of the distal end can be used. Further, in the method where the direction is restricted by the fitting groove within the channel corresponding to the shape of the treatment portion or by the endoscopic attachment on the distal end of the inserted portion, if the treatment portion passes through the corresponding restricting portion so as to project from the distal end of the inserted portion, the restriction is released.

Patent Document 1: Japanese Patent No. 3482022
Patent Document 2: JP-A-H8-168492
Patent Document 3: JP-A-2002-112946
Patent Document 4: JP-A-2000-354581

DISCLOSURE OF THE INVENTION

Problem to be Solved by the Invention

An advantage of the invention is that it provides an endoscopic attachment, an endoscopic treatment instrument, and an endoscope system, which can selectively function only when an endoscopic treatment instrument of which a treatment portion needs to be restricted from being rotated is used, and can serve as a typical endoscope in other cases.

According to an aspect of the invention, an endoscopic attachment includes a cover portion that is mounted on a distal end of an inserted portion of an endoscope so as to cover a portion of an opening portion of a channel formed in the inserted portion of the endoscope; and an endoscope mounting portion that is fixed to the inserted portion of the endoscope. A non-circular deformed hole is formed in the opening portion of the channel by the cover portion, the rotation of an endoscopic treatment instrument, which projects from the opening of the channel and has a non-circular cross-section corresponding to the deformed hole, is restricted by the deformed hole, and the endoscopic treatment instrument freely moves in and out of the opening portion of the channel in a predetermined direction.

In accordance with this aspect, when the endoscopic treatment instrument provided with a flexible tube having a cross-section corresponding to the deformed hole formed by the cover potion is used and projected from the opening portion of the channel where the deformed hole is formed, the deformed hole of the cover portion restricts the flexible tube of the endoscopic treatment instrument from being rotated around the axis of the channel and projects the flexible tube in a predetermined direction.

According to another aspect of the invention, as a non-circular through-hole of which the area is set to be smaller than that of the opening of the channel is formed in the cover portion so as to communicate with the channel, the deformed hole is formed in the opening portion of the channel.

In accordance with this aspect, the flexible tube of the endoscopic treatment instrument is inserted into the non-circular through-hole, formed in the cover portion, from the channel so as to project. Then, the flexible tube of the endoscopic treatment instrument is restricted from being rotated around the axis of the channel and is projected in a predetermined direction.

According to a further aspect of the invention, an endoscope system includes the endoscopic attachment according to the first or second aspect; the endoscopic treatment instrument including a flexible tube having a non-circular cross-section, at least at the distal end thereof, corresponding to the shape of the deformed hole formed by the cover portion of the endoscopic attachment; and a treatment portion that freely moves in and out of the distal end of the flexible tube, is formed in a shape having an orientation around the axis of the flexible tube, and is restricted from being rotated; and the endoscope in which the channel into which the endoscopic treatment instrument can be inserted is provided in the inserted portion.

In accordance with this aspect, the endoscopic attachment having a non-circular deformed hole formed therein and the endoscopic treatment instrument having the flexible tube of which the distal end has a cross-sectional shape corresponding to the non-circular shape are assembled into the endoscope. The flexible tube of the endoscopic treatment instrument is always restricted from being rotated at the distal end of the inserted portion of the endoscope. Therefore, the treatment portion of the endoscopic treatment instrument can always project from the distal end of the flexible tube of the endoscopic treatment instrument in a predetermined direction with respect to the inserted portion of the endoscope so as to perform treatment of an affected area.

Effects of The Invention

According to the invention, as the endoscopic attachment is mounted on a typical endoscope having an opening portion of a channel, a non-circular deformed hole can be formed in the opening portion of the channel. Therefore, when rotation restriction needs to be performed, the endoscope system is used, which is composed of the endoscope, the above-described endoscopic attachment, and the endoscopic treatment instrument having the flexible tube of which the distal end has a cross-section corresponding to the endoscopic attachment. Then, the treatment portion projecting from the opening portion of the channel can be restricted from being rotated. Further, when the endoscopic attachment is removed, the endoscope system can be handled in the same manner as that of a typical endoscope, and a typical endoscopic treatment instrument can be used.

REFERENCE NUMERALS 1, 34, 45: ENDOSCOPE SYSTEM
2: ENDOSCOPE
3: INSERTED PORTION
3a: DISTAL END
4, 23, 24, 30, 35, 46: ENDOSCOPIC ATTACHMENT
5: CHANNEL
5a: OPENING PORTION
6, 40: ENDOSCOPIC TREATMENT INSTRUMENT
7, 26, 36: COVER PORTION
9, 28: MOUNTING PORTION FOR ENDOSCOPE
13, 25, 31, 38: DEFORMED HOLE
14, 41: FLEXIBLE TUBE
14b, 41b: DISTAL END
14d, 41d: PROTRUDING AND RETRACTING PORTION
16, 42: TREATMENT PORTION

BEST MODE FOR CARRYING OUT THE INVENTION (First Embodiment)

Figure 1:
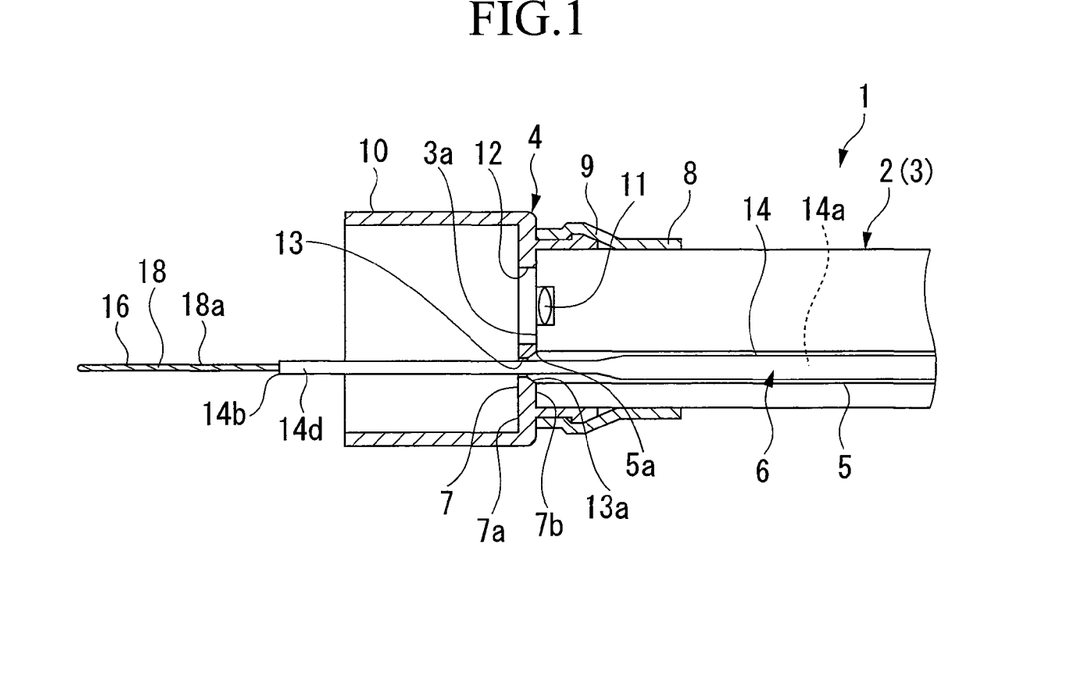
FIG. 1 is a cross-sectional view of an endoscope system according to a first embodiment of the invention.
Figure 2:
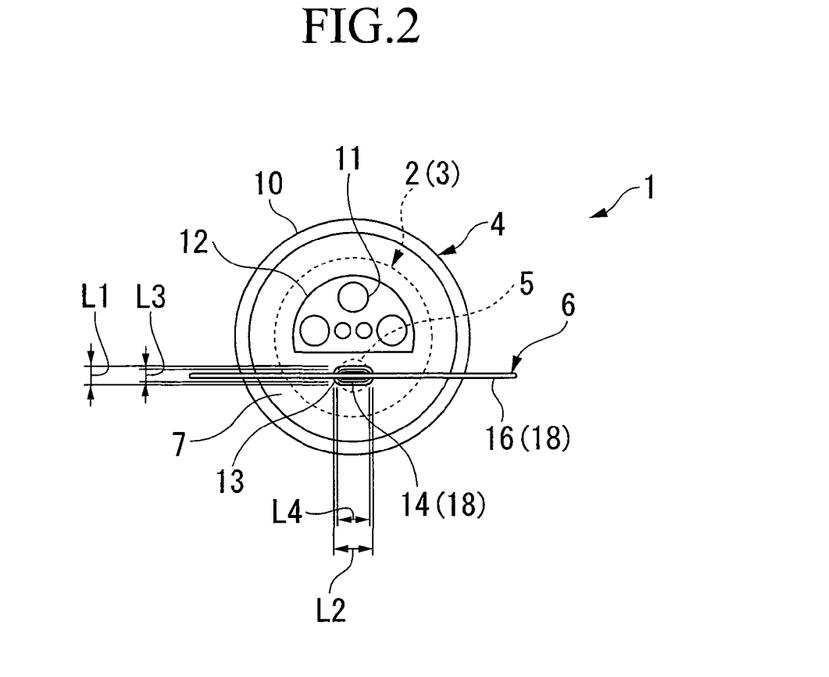
FIG. 2 is a front view of the endoscope system according to the first embodiment of the invention.
Figure 3:
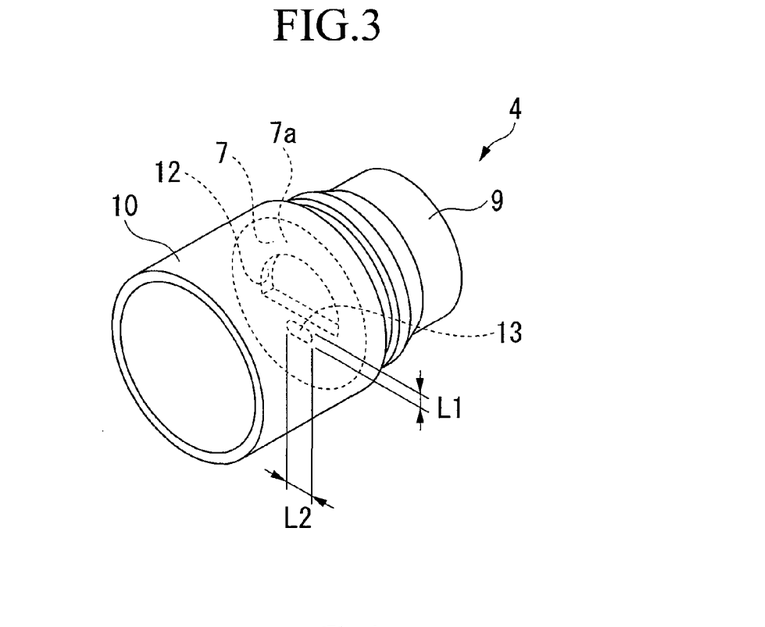
FIG. 3 is a perspective view of an endoscopic attachment according to the first embodiment of the invention.
Figure 4:
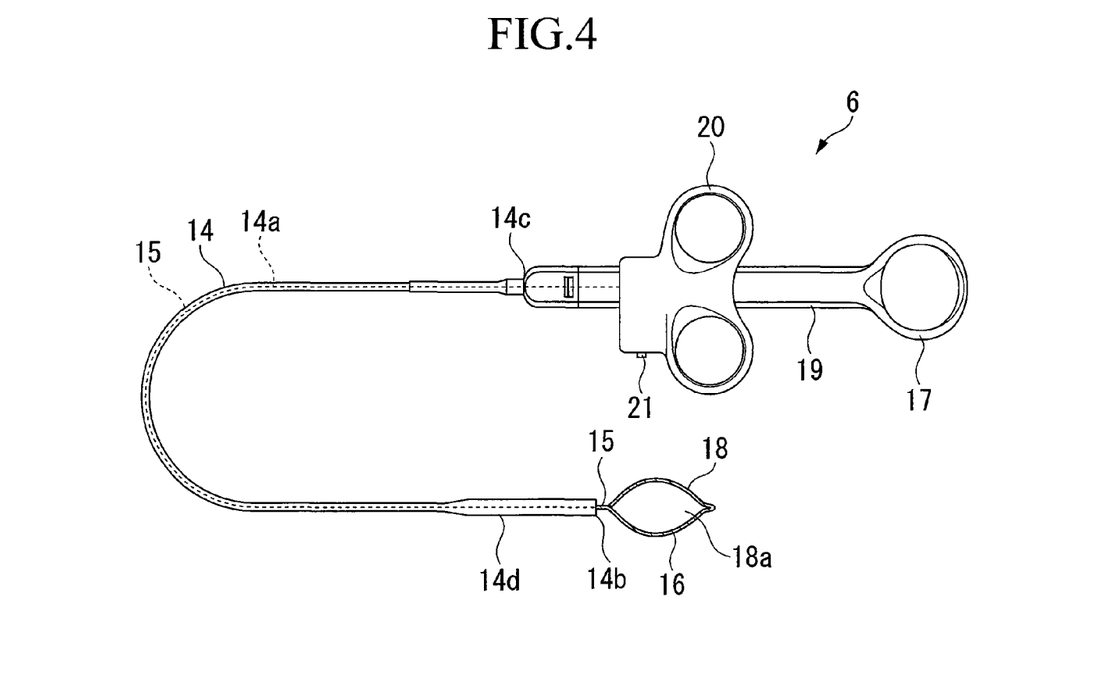
FIG. 4 is an overall view of an endoscopic treatment instrument according to the first embodiment of the invention.
Figure 5:
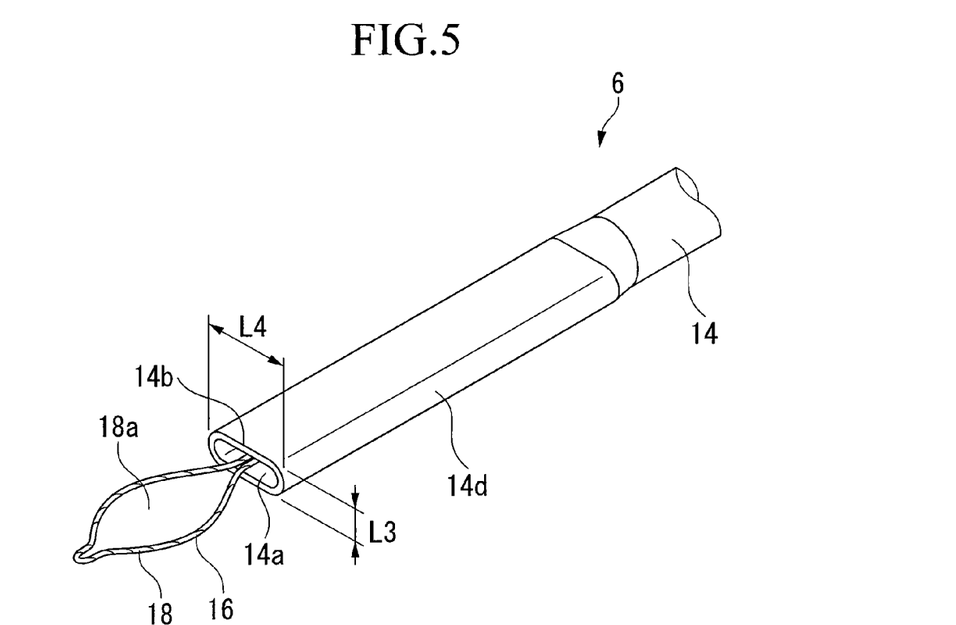
FIG. 5 is an expanded view of a distal end of a flexible tube of the endoscopic treatment instrument according to the first embodiment of the invention.
Figure 6:
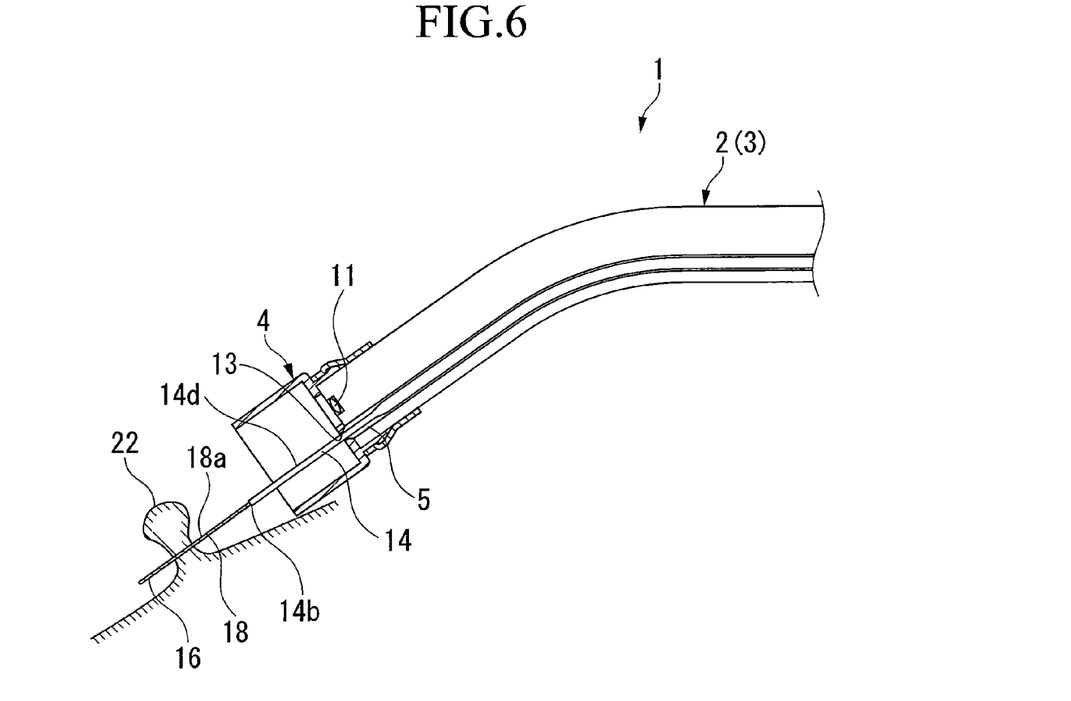
FIGS. 6 and 7 are situation diagrams showing an excision operation of a target portion.
Figure 7:
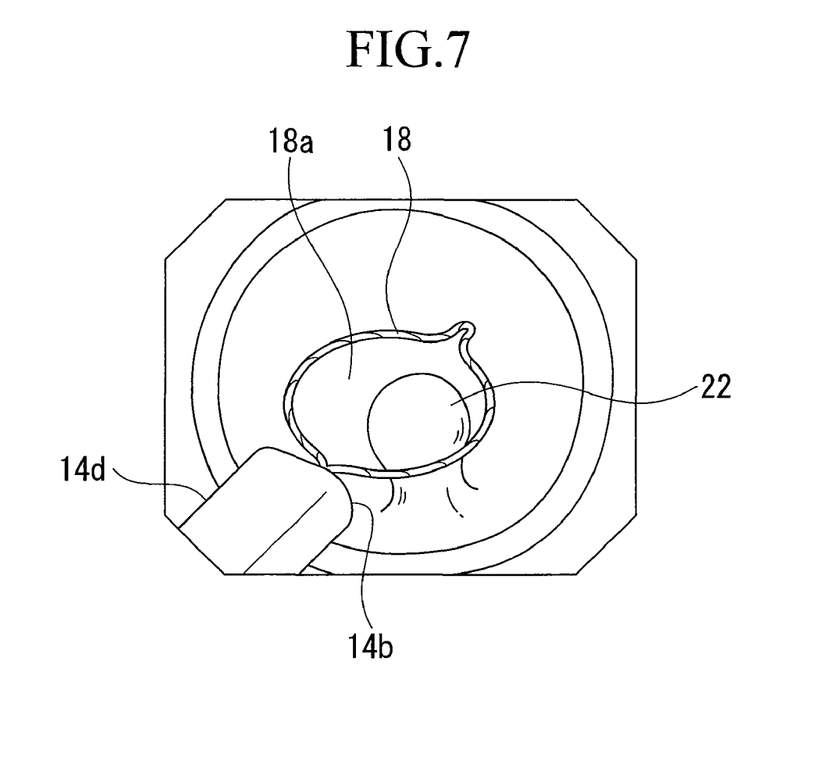

FIGS. 1 to 7 illustrate a first embodiment according to the present invention. FIG. 1 is a cross-sectional view of an endoscope system 1, and FIG. 2 is a front view of the endoscope system 1. FIG. 3 is a perspective view of an endoscopic attachment 4. FIG. 4 is an overall view of an endoscopic treatment instrument 6, and FIG. 5 is an expanded view of a distal end 14b of a flexible tube 14 of the endoscopic treatment instrument 6. FIGS. 6 and 7 are situation diagrams showing a state where the endoscope system 1 is used in a target portion.

As shown in FIG. 1, the endoscope system 1 includes an endoscope 2, an endoscopic attachment 4 mounted on a distal end 3a of an inserted portion 3 of the endoscope 2, and an endoscopic treatment instrument 6 which is inserted into a channel 5 from a base end (not shown) and freely moves in and out of an opening portion 5a of the channel 5 formed at the distal end 3a. The channel 5 passes through the inserted portion 3 of the endoscope 2 from the base end (not shown) to the distal end 3a.

As shown in FIGS. 1 to 3, the endoscopic attachment 4 according to this embodiment includes a cover portion 7 which can cover a portion of the distal end 3a when the endoscopic attachment 4 is mounted on the distal end 3a of the inserted portion 3 of the endoscope 2, an endoscope mounting portion 9 which is attached on the outside of the inserted portion 3 and can be fixed to the distal end 3a of the inserted portion 3 by a fastening ring 8, and a substantially cylindrical cap portion 10 which is provided to project from the outer circumference of the cover portion 7 when the endoscopic attachment 4 is mounted on the distal end 3a of the inserted portion 3. The cover portion 7 has a peephole window 12 and a deformed hole 13 passing therethrough. When the endoscopic attachment 4 is mounted on the distal end 3a of the inserted portion 3, the peephole window 12 corresponds to the position of an observation window 11, and the deformed hole 13 corresponds to the position of the opening portion 5a of the channel 5 positioned under the observation window 11. The opening of the peephole window 12 has such a size that does not affect the observation through the observation window 11. Further, the opening of the deformed hole 13 has a non-circular shape on an outer surface 7a of the cover portion 7 where the cap portion 10 is formed, and the area of the deformed hole 13 is set to be smaller than that of the corresponding opening portion 5a of the channel 5. More specifically, the opening of the deformed hole 13 has a substantially elliptical shape which is elongated in the side-to-side direction rather than in the vertical direction. Further, on an inner surface 7b of the cover 7 in the side where the inserted portion 3 of the endoscope 2 is mounted, a tapered induction portion 13 is formed in the same substantially-circular shape as that of the corresponding opening portion 5a of the channel 5. The induction portion 13a passes through an opening of the outer surface 7a and an opening of the inner surface 7b.

As shown in FIGS. 4 and 5, the endoscopic treatment instrument 6 according to this embodiment includes a flexible tube 14, an operation wire 15 interposed in the inside 14a of the flexible tube 14 so as to freely move, a treatment portion 15 which is connected to a distal end 15a of the operation wire 15 so as to freely move in and out of the distal end 14b of the flexible tube 14 with the movement of the operation wire 15, and an operator 17 which is connected to a base end 14c of the flexible tube 14 and can freely operate the operation wire 15 in the axial direction of the flexible tube 14 in the inside 14a of the flexible 14. A protruding and retracting portion 14d of the flexible tube 14 around the distal end 14b has a non-circular cross-section corresponding to the opening shape of the deformed hole 13 on the outer surface 7a. More specifically, as shown in FIGS. 2, 3, and 5, the minor-axis diameter L3 of the cross-section of the protruding and retracting portion 14d of the flexible tube 14 is set to be smaller than the minor-axis diameter L1 of the elliptical shape of the deformed hole 13 on the outer surface 7a. Further, the major-axis diameter L4 of the cross-section of the protruding and retracting portion 14d of the flexible tube 14 is set to be smaller than the major-axis diameter L2 of the elliptical shape of the deformed hole 13 on the outer surface 7a and is set to be larger than the minor-axis length L1. In this embodiment, a high-frequency snare is used as the treatment portion 16. The high-frequency snare has a substantially circular and elastic snare loop 18 connected to the distal end 15a of the operation wire 15 such that a high-frequency current can flow in the snare loop 18 through the operation wire 15 from the operator 17. When the high-frequency snare serving as the treatment portion 16 projects from the distal end 14b of the flexible tube 14, the high-frequency snare is restricted from being rotated in a direction where a loop surface 18a of the snare loop 18 coincides with the major-axis diameter of the cross-section of the protruding and retracting portion of the flexible tube 14. The operator 17 includes a base part 19, a slider 20 which freely slides on the base part 19 with respect to one axis and is interlocked with the operation wire 15, and an electrode 21 which is capable of flowing a high-frequency current into the operation wire 15.

Next, the operation of the endoscope system 1 of this embodiment will be described. As shown in FIG. 1, the endoscopic attachment 4 is mounted on the distal end 3a of the inserted portion 3 of the endoscope 2. The endoscope mounting portion 9 of the endoscopic attachment 4 is attached to the outside of the inserted portion 3, and the inner surface 7b of the cover portion 7 is abutted on the distal end 3a of the inserted portion 3 so as to be fixed to the outer circumference of the inserted portion 3 through the fastening ring 8. At this time, as shown in FIG. 2, the positions of the observation window 11 and the peephole window 12 of the cover portion 7 coincide with each other, and the observation window 11 is exposed from the outside of the distal end 3a of the inserted portion 3. Further, the position of the endoscopic attachment 4 is adjusted in such a manner that the deformed hole 13 of the cover portion 7 and the opening portion 5a of the channel 5 communicate with each other.

In this state, the deformed hole 13 of the cover portion 7 has a substantially elliptical shape, which is elongated in the side-to-side direction rather than in the vertical direction, in the positional relationship where the deformed hole 13 is positioned under the observation window 11.

In this state, the distal end 3a of the inserted portion 3 of the endoscope 2 is inserted into a body such that the inserted portion 3 of the endoscope 2 approaches a target portion inside the body.

When the inserted portion 3 of the endoscope 2 approaches the target portion, the distal end 14b of the flexible tube 14 of the endoscopic treatment instrument 6 is inserted into the channel 5 from the base end (not shown) of the inserted portion 3 of the endoscope 2, as shown in FIG. 1. As shown in FIG. 2, the distal end 14b of the flexible tube 14 which has approached the vicinity of the opening portion 5a of the channel 5 is rotated around the axis of the channel 5 along the induction portion 13a of the deformed hole 13 which is formed in the opening 5b such that the orientation of the deformed hole 13 and the orientation of the cross-section of the protruding and retracting portion 14d of the flexible tube 14 become the same direction around the axis of the channel 5. Then, the distal end 14b of the flexible tube 14 projects from the deformed hole 13. In this state where the distal end 14b projects, the rotation of the flexible tube 14 around the axis of the channel 5 is restricted by the shape of the deformed hole 13 and the cross-sectional shape of the protruding and retracting portion 14d of the flexible tube 14. The deformed hole 13 has an elliptical shape which is elongated in the side-to-side direction rather than in the vertical direction. Therefore, as the major-axis direction of the cross-section of the protruding and retracting portion 14d of the flexible tube 14 is caused to coincide with the loop surface 18a of the snare loop 18 of the treatment portion 16, the orientation of the treatment portion 16, which projects into the target portion so as to perform treatment, is directed in such a manner that the rotation of the loop surface 18a is restricted in the vertical direction. Further, the observation window 11 is disposed upwardly with respect to the opening portion 5a of the channel 5. Therefore, in this state, the loop surface 18a can be seen in a planar view from the top through the observation window 11.

FIGS. 6 and 7 show an excision operation of a polyp 22 which is a target portion. As described above, the rotation of the loop surface 18a is restricted in the vertical direction, and the loop surface 18a and the polyp 22 can be seen in a planar view from the top through the observation window 11. Therefore, the polyp 22 can be easily captured into the inside of the snare loop 18. In this state, the slider 20 of the operator 17 shown in FIG. 4 is operated in such a manner that the operation wire 15 is drawn to the side of the base end 14c of the flexible tube 14. Accordingly, the snare loop 18 can be narrowed to tighten the polyp 22. At this time, the treatment portion 16 is rotated around the axis of the channel 5 such that a stabilized operation can be performed without the snare loop 18 coming off from the polyp 22. In this state, when a high-frequency current flows into the snare loop 18 through the electrode 21 of the operator 17, it is possible to excise the polyp 22.

As such, in the endoscope system 1 of this embodiment, the treatment operation can be realized in a state where the rotation of the treatment portion 16 is restricted. When the length of the protruding and retracting portion 14d of the flexible tube 14 having a non-circular cross-section is set to be larger than that of the flexible tube 14 projecting from the opening portion 5a of the channel 5, the rotation-restricted state of the treatment portion 15 can be always maintained while the treatment operation is performed. Further, when the endoscopic attachment 4 is removed, a typical method can be also used by the endoscope 2 and a conventional endoscopic treatment instrument of which the flexible tube 14 has a circular cross-section.

Figure 8:
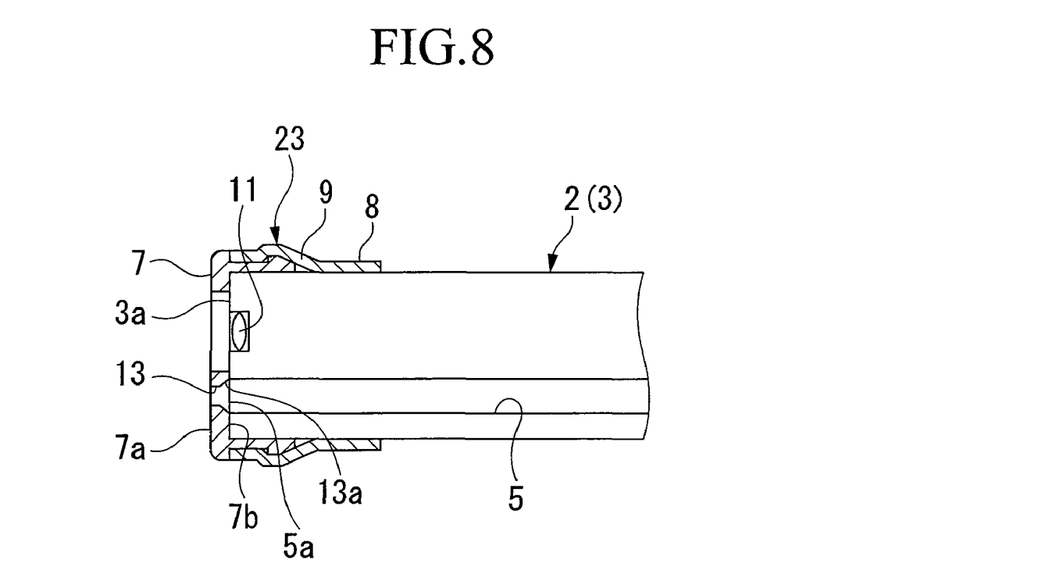
FIG. 8 is a cross-sectional view of an endoscope system according to a first modification of the invention.
Figure 9:
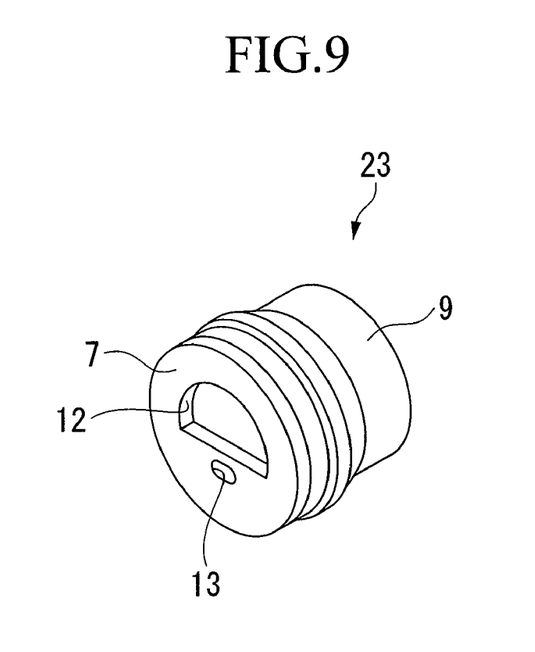
FIG. 9 is a perspective view of the endoscope system according to the first modification of the invention.

FIGS. 8 and 9 illustrate a first modification of the endoscopic attachment of this embodiment. FIG. 8 is a cross-sectional view of an endoscopic attachment 23 according to this modification, showing a state where the endoscopic attachment 23 is mounted on the endoscope 2. FIG. 9 is a perspective view of the endoscopic attachment 23. This modification shows an example where the cap portion 10 is not provided in the endoscopic attachment 4 shown in FIG. 3. The cap portion 10 may be omitted as in this modification, except for when a target portion is aspired, or when an excised portion is collected.

Figure 10:
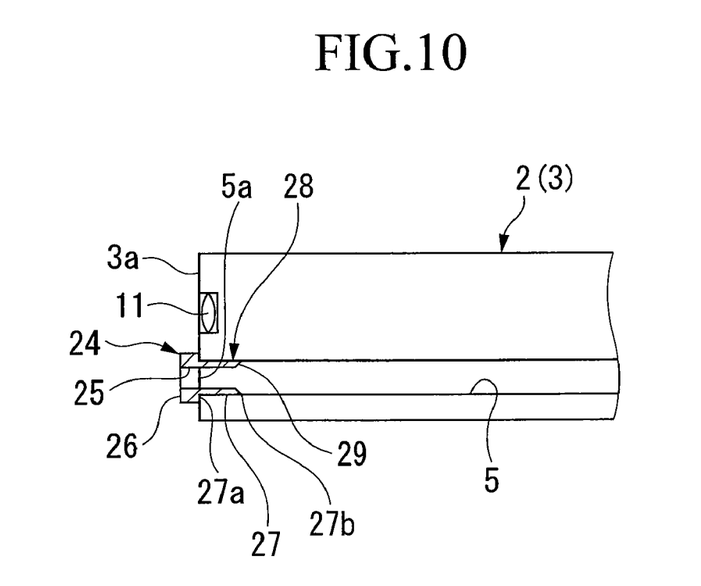
FIG. 10 is a cross-sectional view of an endoscope system according to a second modification of the invention.
Figure 11:
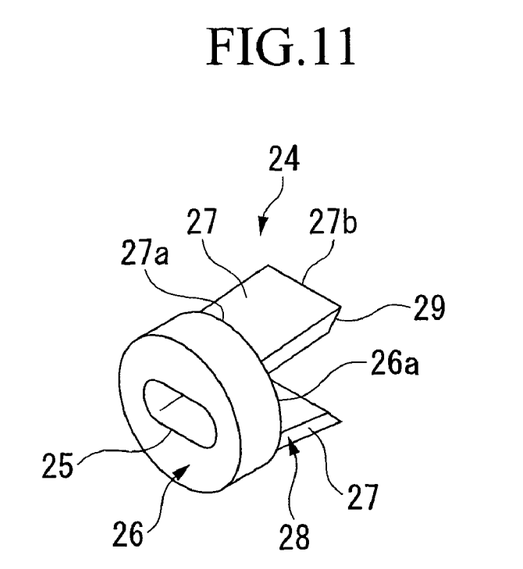
FIG. 11 is a perspective view of the endoscope system according to the second modification of the invention.

FIGS. 10 and 11 illustrate a second modification of the endoscopic attachment of this embodiment. FIG. 10 is a cross-sectional view of an endoscopic attachment 24 according to this modification, showing a state where the endoscopic attachment 24 is mounted on the inserted portion 3 of the endoscope 2, and FIG. 11 is a perspective view of the endoscopic attachment 24. The endoscopic attachment 24 of this modification is a substantially plate-shaped member which covers only the periphery of the opening portion 5a of the channel 5 in the distal end 3a of the inserted portion 3 of the endoscope 2. The endoscopic attachment 24 includes a cover portion 26 having a deformed hole 25 and a mounting portion 28 having two elastic mounting plates 27. The deformed hole 25, of which the area is set to be smaller than that of the opening portion 5a of the channel 5, is a hole formed in a substantially elliptical shape which is elongated in the side-to-side direction rather than in the vertical direction, the deformed hole 25 passing through the cover portion 26. The mounting plates 27 are bonded to the inner surface 26a of the cover portion 26 above and under the opening portion of the deformed hole 25. A distance between the mounting plates 27 increases from one end 27a of each of the mounting plates 27, bonded to the cover portion 26, to the other end 27b thereof. Each of the mounting plates 27 has a tapered induction portion 29 formed at the other end 27b thereof. As shown in FIG. 10, the endoscopic attachment 24 of this modification is fixed by inserting the mounting plates 27 of the mounting portion 28 into the channel 5. The mounting plates 27 are abutted on the inner surface of the channel 5 by the elasticity thereof. Further, the endoscopic treatment instrument (not shown) inserted into the channel 5 is induced into the deformed hole 25 by the induction portions 29 formed on the mounting plates 27. In this modification, the endoscopic attachment covers only the opening portion 5a of the channel 5. However, this does not matter, because the rotation of the endoscopic treatment instrument (not shown) is restricted in the same manner by the deformed hole 25.

(Second Embodiment)

Figure 12:
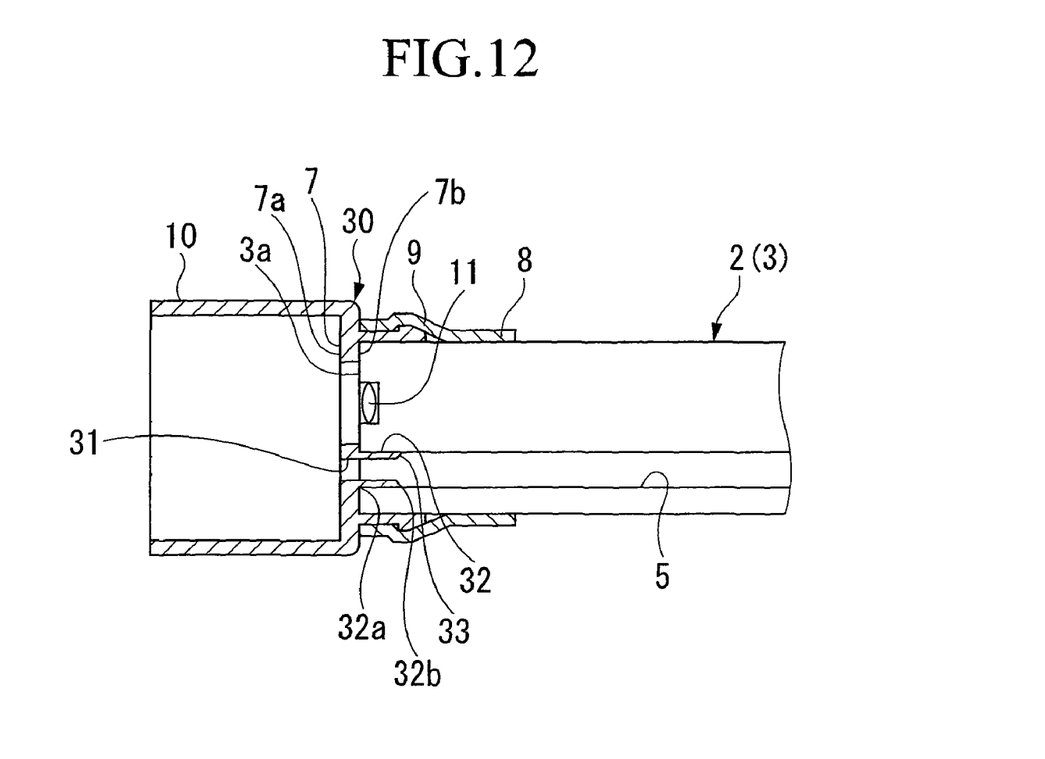
FIG. 12 is a cross-sectional view of an endoscope system according to a second embodiment of the invention.

FIG. 12 is a cross-sectional view of a second embodiment according to the invention. In this embodiment, like reference numerals are attached to the same components as those of the above-described embodiment, and the descriptions thereof will be omitted. In an endoscopic attachment 30 of this embodiment, the area of a deformed hole 31 passing through the cover portion 7 is set to be smaller than that of the opening portion 5a of the channel 5, and the deformed hole 31 is formed in a substantially elliptical shape which is elongated in the side-to-side direction rather than in the vertical direction. Further, guide members 32 are bonded to the inner surface 7b of the cover portion 7 above and under the opening portion of the deformed hole 3. When the endoscopic attachment 30 is mounted on the distal end 3a of the inserted portion 3 of the endoscope 2, the guide members 32 are abutted on the inner surface of the channel 5. One end 32a of each of the guide members 32 is bonded to the cover portion 7, and the other end 32b of each of the guide members 32 respectively has a tapered induction portion 33 formed thereon. When the endoscopic attachment 30 of this embodiment is mounted on the distal end 3a of the inserted portion 3 of the endoscope 2, the guide members 32 are inserted into the channel 5. Therefore, it is easy to position the endoscope 2 in a position where the deformed hole 31 and the opening portion 5a of the channel 5 communicate with each other. Further, since the induction portions 33 are formed, it is possible to easily induce the endoscopic treatment instrument (not shown), which is inserted into the channel 5, into the deformed hole 31.

(Third Embodiment)

Figure 13:
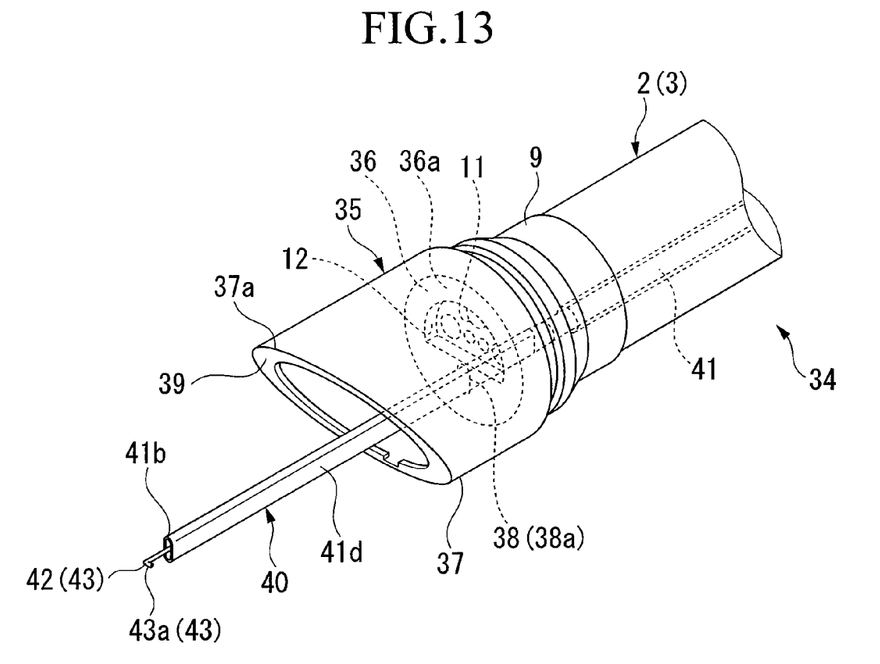
FIG. 13 is a perspective view of an endoscope system according to a third embodiment of the invention.
Figure 14:
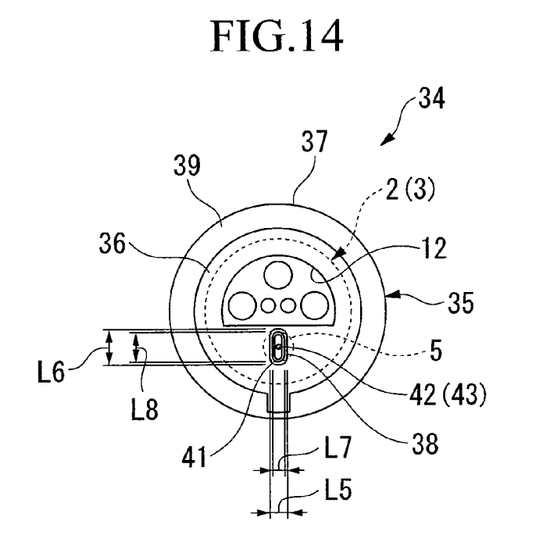
FIG. 14 is a front view of an endoscope system according to the third embodiment of the invention.
Figure 15:
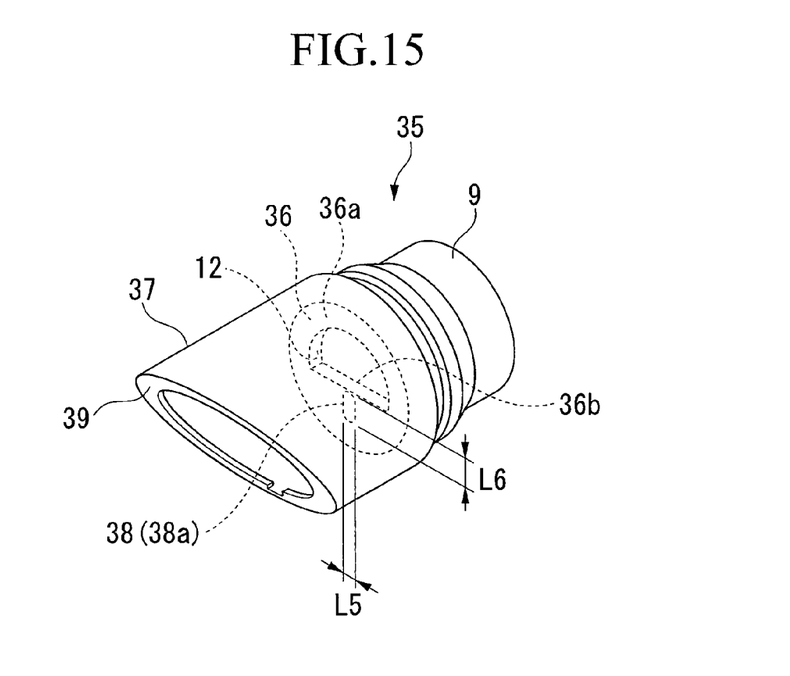
FIG. 15 is a perspective view of an endoscopic attachment according to the third embodiment of the invention.
Figure 16:
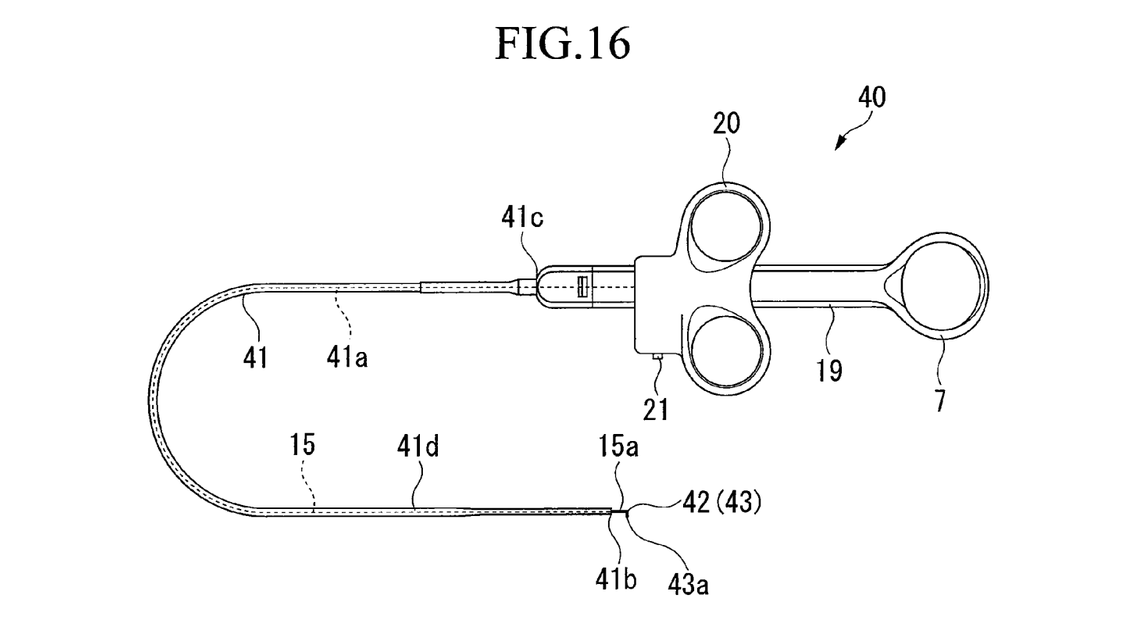
FIG. 16 is an overall view of an endoscopic treatment instrument according to the third embodiment of the invention.
Figure 17:
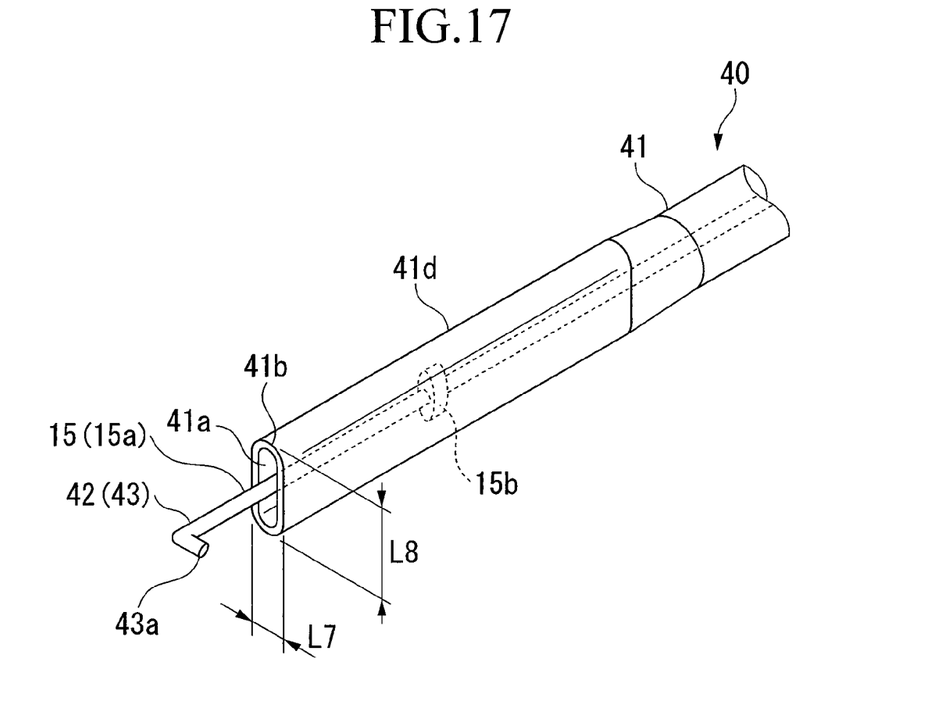
FIG. 17 is an expanded view of a distal end of a flexible tube of the endoscopic treatment instrument according to the third embodiment of the invention.
Figure 18:
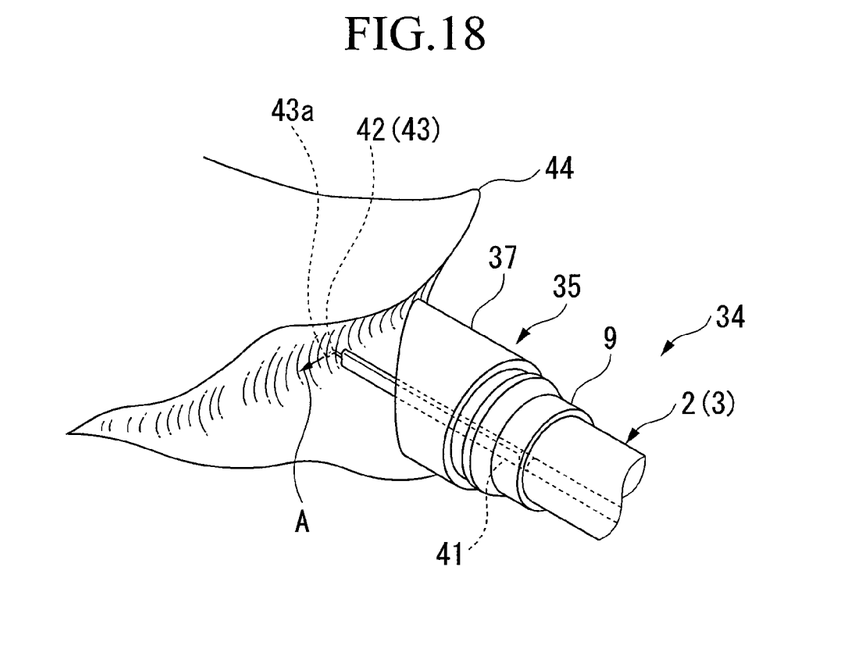
FIG. 18 is a condition diagram showing an excision operation of a target portion.

FIGS. 13 to 18 illustrate a third embodiment according to the invention. In this embodiment, like reference numerals are attached to the same components as those of the above-described embodiments, and the descriptions thereof will be omitted. FIG. 13 is a perspective view of an endoscope system 34 of this embodiment, and FIG. 14 is a front view of the endoscope system 34. FIG. 15 is a perspective view of an endoscopic attachment 35. FIG. 16 is an overall view of an endoscopic treatment instrument 40. FIG. 17 is an expanded view of a distal end 41 of a flexible tube 41 of the endoscopic treatment instrument 40. FIG. 18 is a condition diagram showing a state where the endoscope system 34 is used in a target portion.

As shown in FIGS. 13 to 15, the endoscopic attachment 35 of the endoscope system 34 of this embodiment includes a cover portion 36, a cap portion 37, and an endoscope mounting portion 9. The cover portion 36 has a deformed hole 38 passing therethrough. The area of the deformed hole 38 on an outer surface 36a is set to be smaller than that of the opening portion 5a of the channel 5, and the deformed hole 38 has a substantially elliptical shape which is elongated in the side-to-side direction rather than in the vertical direction. Further, a tapered induction portion 38a having the same shape as the opening portion 5a of the channel 5 is formed from the inner surface 36b of the cover portion 36, the induction portion 38a passing through the outer surface 36a and the inner surface 36b. The cap portion 37 is a cover which is formed in a substantially cylindrical shape so as to project on the outer circumference of the cover portion 36. The surface of a distal end 37a of the cap portion 37 is formed obliquely with respect to the cover potion 36. Further, a nail portion 39 projecting in an inner circumferential direction is formed on the entire circumference of the distal end 37a.

As shown in FIGS. 16 and 17, the endoscopic treatment instrument 40 of this embodiment includes a flexible tube 41, an operation wire 15 which is interposed in the inside 41a of the flexible tube 41 so as to freely move, a treatment portion 42 which is connected to the distal end 15a of the operation wire 15 and is interlocked with the operation wire so as to freely move in and out of the distal end 41b of the flexible tube 41, and the operator 17 which is connected to a base end 41c of the flexible tube 41 and can freely operate the operation wire 15 in the axial direction of the flexible tube 41 in the inside 41a of the flexible 41.

A protruding and retracting portion 41d of the flexible tube 41 has a non-circular shape corresponding to the opening shape of the deformed hole 38 on the outer surface 36a. More specifically, as shown in FIG. 14, the minor-axis diameter L7 of the cross-section of the protruding and retracting portion 41d of the flexible tube 41 is set to be smaller than the minor-axis diameter L5 of the elliptical shape of the deformed hole 38 on the outer surface 36a. Further, the major-axis diameter L8 of the cross-section of the protruding and retracting portion 41d of the flexible tube 41 is set to be smaller than the major-axis diameter L6 of the elliptical shape of the deformed hole 38 on the outer surface 36a and is set to be larger than the minor-axis diameter L5. In this embodiment, a hook-shaped knife 43 is used as the treatment portion 42. Further, a rotation restricting member 15b is provided on the operation wire 15 at the base end rather than at the treatment portion 42. The rotation restricting member 15b has such a size that can be housed in the protruding and retracting portion 41d of the flexible tube 41 and has a substantially elliptical cross-section corresponding to the cross-section of the protruding and retracting portion 41d. Further, the minor-diameter direction of the elliptical cross-section of the rotation restricting member 15b coincides with the direction of an L-shaped distal end 43a of the hook-shaped knife 43 of the treatment portion 42. Further, a high-frequency current can flow into the distal end 43a of the hook-shaped knife 43 through the operation wire 15 by the electrode 21 of the operator 17.

Next, the operation of the endoscope system 34 of this embodiment will be described. Similar to the first embodiment, the endoscopic attachment 35 is mounted on the distal end 3a of the inserted portion 3 of the endoscope 2. In this state, the distal end 3a of the inserted portion 3 of the endoscope 2 is inserted into a body such that the inserted portion 3 approaches a target portion of the body. When the inserted portion 3 approaches the target portion, the distal end 41b of the flexible tube 41 of the endoscopic treatment instrument 40 is inserted into the channel 5 from the base end (not shown) of the inserted portion 3 of the endoscope 2, as shown in FIG. 13. The distal end 41b of the flexible tube 41 which has approached the vicinity of the opening portion 5a of the channel 5 is rotated around the axis of the channel 5 along the induction portion 38a of the deformed hole 38 which is formed in the opening 5b of the channel 5 such that the orientation of the deformed hole 38 and the orientation of the cross-section of the protruding and retracting portion 41d of the flexible tube 41 become the same direction around the axis of the channel 5. Then, the distal end 41b of the flexible tube 41 projects from the deformed hole 13. In this state where the distal end 41b projects, the rotation of the flexible tube 41 around the axis of the channel 5 is restricted by the shape of the deformed hole 38 and the cross-sectional shape of the protruding and retracting portion 41d of the flexible tube 41.

The deformed hole 38 has an elliptical shape which is elongated in the side-to-side direction rather than in the vertical direction, and the minor-diameter direction of the cross-section of the protruding and retracting portion 41d of the flexible tube 41 is caused to coincide with the direction of the distal end 43a of the hook-shaped knife 43 of the treatment portion 42 by the rotation restricting member 15b of the operation wire 15. Therefore, the rotation of the treatment portion 42, which projects into the target portion so as to perform treatment, is restricted in such a manner that the distal end 43a of the hook-shaped knife 43 is directed to a lateral direction.

FIG. 18 illustrates an excision operation of a lesioned mucosa 44 which is a target portion. As described above, the rotation of the treatment portion 42 is restricted in such a manner that the distal end 43a of the hook-shaped knife 43 is maintained in a lateral direction. Therefore, it is possible to easily excise the lesioned mucosa 44 in a cutting direction A.

Although the third embodiment has been described so far, the cap portion 37 is formed in such a manner that the surface of the distal end 37a becomes parallel to the cover portion 36 as in the first embodiment, depending on the use. Further, the nail portion 39 may be omitted.

(Fourth Embodiment)

Figure 19:
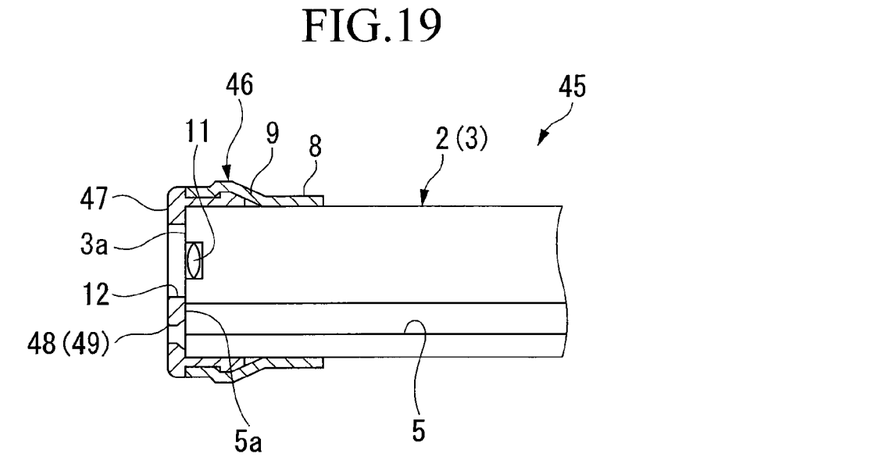
FIG. 19 is a cross-sectional view of an endoscope system according to a fourth embodiment of the invention.
Figure 20:
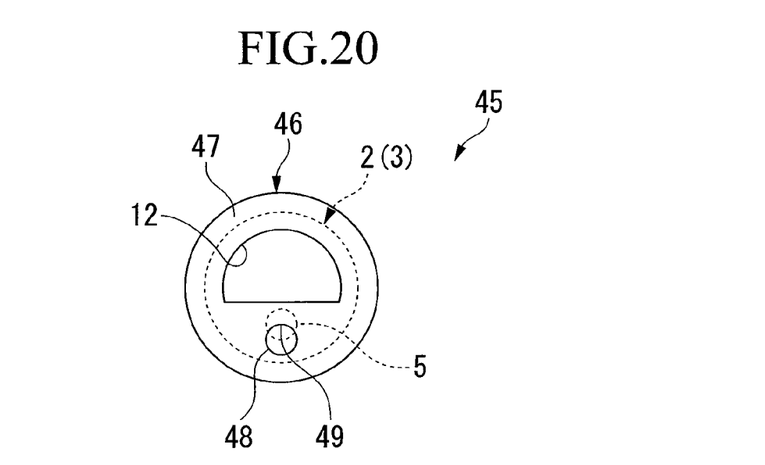
FIG. 20 is a front view of the endoscope system according to the fourth embodiment of the invention.
Figure 21:
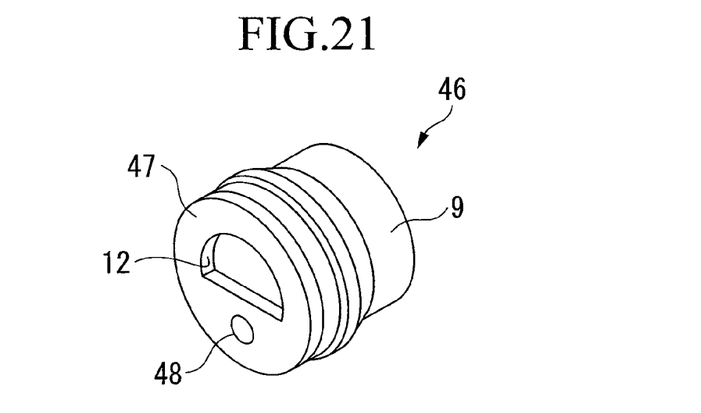
FIG. 21 is a perspective view of an endoscopic attachment according to the fourth embodiment of the invention.

FIGS. 19 to 21 illustrate a fourth embodiment according to the invention. In this embodiment, like reference numerals are attached to the same components as those of the above-described embodiments, and the descriptions thereof will be omitted. FIG. 19 is a cross-sectional view of an endoscope system 45, FIG. 20 is a front view of the endoscope system 45, and FIG. 21 is a perspective view of an endoscopic attachment 46.

As shown in FIG. 19, the endoscopic attachment 46 of this embodiment includes a cover portion 47, which covers the distal end 3a of the inserted portion 3 of the endoscope 2, and the endoscope mounting portion 9. The cover portion 47 has two through-holes such as a peephole window 12 and a circular hole 48 formed therein. As shown in FIGS. 19 and 20, the circular hole 48 is disposed in an eccentric position with the opening portion 5a of the channel 5, when the endoscopic attachment 46 is mounted on the distal end 3a of the inserted portion 3 of the endoscope 2. Therefore, a deformed hole 49 is formed by the circular hole 48 of the cover portion 47 and the opening portion 5a of the channel 5. When the endoscopic treatment instrument (not shown) is provided with a flexible tube (not shown) having a distal end with a cross-section which fits into the deformed hole 49, it is possible to obtain the same rotation-restriction effect.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

In this embodiment, the high-frequency snare and the hook-shaped knife are used as the treatment portion. Without being limited thereto, various endoscopic treatment instruments such as a straight grasping forceps or a basket forceps can be used. Further, the deformed hole formed by the cover portion is formed in a substantially elliptical shape. Without being limited thereto, the deformed hole may be formed in any non-circular shape which is capable of restricting rotation.

(Additional Aspect 1)

The endoscopic attachment according to the first aspect further including a substantially circular cap portion which projects from the distal end of the cover portion.

(Additional Aspect 2)

The endoscopic attachment according to the first aspect, wherein the deformed hole has a tapered induction portion formed therein, the induction portion inducing the flexible tube which is inserted into the channel of the endoscope.

(Additional Aspect 3)

The endoscopic attachment according to the first aspect further including guide members that are formed on the periphery of the deformed hole on the inner surface of the cover portion, which is abutted on the distal end of the inserted portion of the endoscope, and are abutted on the inner surface of the channel when the endoscopic attachment is mounted in the inserted portion of the endoscope.

As such, as the substantially cylindrical cap portion is provided to project from the outer circumference of the cover portion, a target portion can be aspired and introduced into the inside, or the cap portion can serve as an endoscopic hood.

As the tapered induction portion is provided in the deformed hole formed in the cover portion, the flexible tube can be inserted into the deformed hole from the channel without resistance.

Further, as the guide members are provided on the inner surface of the cover portion, the endoscopic attachment can be mounted by easily communicating the deformed hole formed in the cover portion with the opening portion of the channel at the distal end of the inserted portion of the endoscope.

The invention claimed is:

1. An endoscopic attachment comprising:
    a cover portion that is mounted on a distal end of an inserted portion of an endoscope so as to cover a portion of an opening portion of a channel formed in the inserted portion of the endoscope; and
    an endoscope mounting portion that is fixed to the inserted portion of the endoscope,
    wherein a non-circular deformed hole is formed in the opening portion of the channel by the cover portion,
    the cover portion includes a tapered induction portion which has a same circular cross section as the opening of the channel to induce an endoscopic treatment instrument which has a non-circular cross-section corresponding to the deformed hole from the channel to the non-circular deformed hole,
    the non-circular deformed hole is configured to have a shape capable of being fitted to an endoscopic treatment instrument, which projects from the opening of the channel and has a non-circular cross section corresponding to the non-circular deformed hole,
    the rotation of the endoscopic treatment instrument is restricted by a fitting of the non-circular cross section in which the endoscopic treatment instrument has with the non-circular deformed hole, and
    the endoscopic treatment instrument freely moves in and out of the opening portion of the channel in a predetermined direction while the rotation of the endoscopic treatment instrument is restricted.

2. The endoscopic attachment according to claim 1, wherein as a non-circular through-hole of which the area is set to be smaller than that of the opening of the channel is formed in the cover portion so as to communicate with the channel, the deformed hole is formed in the opening portion of the channel.

3. An endoscope system comprising:
    the endoscopic attachment according to claim 2;
    the endoscopic treatment instrument including:
        a flexible tube having a non-circular cross-section, at least at the distal end thereof, corresponding to the shape of the deformed hole formed by the cover portion of the endoscopic attachment; and
        a treatment portion that freely moves in and out of the distal end of the flexible tube, that is formed in a shape having an orientation around the axis of the flexible tube, and is restricted from being rotated; and
    the endoscope in which the channel into which the endoscopic treatment instrument can be inserted is provided in the inserted portion.

4. An endoscope system comprising:
    the endoscopic attachment according to claim 1;
    the endoscopic treatment instrument including:
        a flexible tube having a non-circular cross-section, at least at the distal end thereof, corresponding to the shape of the deformed hole formed by the cover portion of the endoscopic attachment; and
        a treatment portion that freely moves in and out of the distal end of the flexible tube, that is formed in a shape having an orientation around the axis of the flexible tube, and is restricted from being rotated; and
    the endoscope in which the channel into which the endoscopic treatment instrument can be inserted is provided in the inserted portion.

* * * * *

UNITED STATES PATENT AND TRADEMARK OFFICE
CERTIFICATE OF CORRECTION

PATENT NO. : 8,357,082 B2
APPLICATION NO. : 11/911279
DATED : January 22, 2013
INVENTOR(S) : Tsutomu Okada It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1292 days.

Signed and Sealed this
First Day of September, 2015

Michelle K. Lee
*Director of the United States Patent and Trademark Office*